(12) United States Patent
Wright et al.

(10) Patent No.: US 6,660,469 B1
(45) Date of Patent: Dec. 9, 2003

(54) APPARATUS AND METHOD TESTING A BIOLOGICAL FLUID

(75) Inventors: David Kent Wright, Leominster (GB); Philip Stephen Fullam, San Antonio, TX (US)

(73) Assignee: Krysium Advisors Limited, Leominster (GB)

(*) Notice: Subject to any disclaimer, the term of this patent is extended or adjusted under 35 U.S.C. 154(b) by 0 days.

(21) Appl. No.: 10/031,869

(22) PCT Filed: May 16, 2000

(86) PCT No.: PCT/GB00/01868

§ 371 (c)(1),
(2), (4) Date: Nov. 13, 2001

(87) PCT Pub. No.: WO00/70011

PCT Pub. Date: Nov. 23, 2000

(30) Foreign Application Priority Data

May 18, 1999  (GB) ............................................. 9911400

(51) Int. Cl.$^7$ ................................................ C12Q 1/00
(52) U.S. Cl. ........................ 435/4; 422/56; 220/203.08
(58) Field of Search ............................. 422/50, 55, 56; 435/4, 7.1; 436/810; 220/203.08

(56) References Cited

U.S. PATENT DOCUMENTS 5,827,675 A   10/1998   Skiffington et al.

FOREIGN PATENT DOCUMENTS

| GB | 2 001 434 A | | 1/1979 | |
|----|---|---|---|---|
| GB | 2 223 095 A | | 3/1990 | |
| GB | 2 281 966 A | | 3/1995 | |
| GB | 2281966 A | * | 3/1995 | .......... G01N/21/01 |
| WO | WO 93/09431 | | 5/1993 | |
| WO | WO 97/03209 | * | 1/1997 | ............. C12Q/1/66 |
| WO | WO 98/37229 | * | 8/1998 | ............. C12Q/1/66 |

* cited by examiner

*Primary Examiner*—Ralph Gitomer
(74) *Attorney, Agent, or Firm*—Kirschstein, et al.

(57) ABSTRACT

An apparatus for testing a biological fluid from an animal for the presence of disease in the animal. The apparatus including a container, a dipstick and a luminometer. One end of the dipstick is inserted into a sample of the fluid so that a predetermined amount of the sample becomes attached to the dipstick and takes part in a reaction in the container which produces light emissions. The luminometer receives the container and is operated whereby a determination of the level of bacteria in the sample and hence of disease in the animal is made, by sensing the light emissions from the container.

10 Claims, 2 Drawing Sheets

APPARATUS AND METHOD TESTING A BIOLOGICAL FLUID

BACKGROUND OF THE INVENTION

This invention relates to an apparatus and method of testing a biological fluid.

It is known to test milk produced by dairy cows and other mammals to determine whether the animal is suffering from mastitis. For example, laboratory testing of milk samples taken by milk collection operatives is regularly carried out.

Known such tests involve either determining the number of bacteria cells in the sample for a direct indication of the presence of mastitis, or determining the number of somatic cells, e.g. tissue, blood or other cells, in the sample to provide an indirect indication of the presence of mastitis in the animal. This latter test relies on the fact that in an animal with an infection such as mastitis white blood cells (leukocytes) produced by the animal's immune system will be transferred into the animal's milk to combat the pathogens. So a high level of somatic cells in the sample will indicate that an infection is present in the animal.

A problem with known laboratory based testing is that there is inevitably a delay between when the sample is taken and when the test results are available. Mastitis can progress rapidly and so the test results may not be accurately indicative of the state of the disease when for example the animal is next milked. Also a laboratory based test on a sample taken by a collection operative (tanker driver), is most likely to include milk produced by a plurality of animals. Thus such tests, whilst being of some use in determining milk quality from a particular farm, are not useful in advising a dairyman for example, as to which of his animals is suffering from mastitis.

Thus a dairyman needs to be able to perform tests on individual animals which will give a rapid result, so that the dairyman can be alerted to an animal which is suffering from mastitis. In response, the dairyman may decide to dispose of an individual animal's milk so as not to lower the quality of milk from the herd, and may make a decision either to treat the animal e.g. with antibiotics, or to allow the animal's own immune system to combat the infection.

In each case, early diagnosis of mastitis is important to enable the dairyman proactively to maintain the quality of the herd's milk provided for production, and to provide for timely, appropriate treatment of individual animals in the herd.

Milk tests are known which are intended to be performed by a dairyman, which are known as the Californian Mastitis Test (CMT) and the conductivity test. However to perform such tests, the tester needs to make subjective judgements which a dairyman may not be sufficiently skilled to make. Also such tests exhibit a lack of sensitivity for detecting subclinical mastitis, and the CMT lacks accuracy at somatic cell count levels required by current rules and regulations. Such tests do not readily lend themselves to use in the context of a cowshed where cows may be milked.

Portable biological fluid testing kits are known, for example from U.S. Pat. No. 5,827,675 but these are complex to use and do not lend themselves readily for use by say, a dairyman, in the field.

SUMMARY OF THE INVENTION

According to one aspect of the invention we provide an apparatus for testing a biological sample from an animal for the presence of disease in the animal, the apparatus including a container, a dipstick and a luminometer, an end of the dipstick being adapted to be inserted into the sample so that a predetermined amount of the sample becomes attached to the dipstick and takes part in a reaction in the container which produces light emissions, the luminometer being adapted to receive the container and to be operated whereby a determination of the level of bacteria and/or somatic cells in the sample and hence of the disease in the animal is made, by sensing light emissions from the container.

The invention has been primarily but not exclusively developed for use in testing raw milk.

Thus utilising an apparatus in accordance with the invention, milk from an individual milk producing animal can be tested by, for example, a dairyman as soon as or soon after the milk is produced, simply, and because the luminometer is capable of measuring light emissions from the container, testing does not rely on subjective determinations.

In order that a luminometer may be used, it is essential that the milk or other fluid attached to the dipstick reacts with an agent on the dipstick and/or the reagent in the container to create a light producing reaction. The amount of light produced preferably is determined by the number of somatic cells in the milk attached to the dipstick whereby the test is an indirect test, i.e. the presence of disease in the animal is indicated by the number of somatic cells in the sample rather than the number of bacterial cells in the sample. However the invention may be applied to direct testing methods which test for bacterial cells in the sample, using a suitable reagent.

Preferably the container contains an extractant and the contents of the somatic cells in the milk or other fluid attached to the dipstick is released on contact with the extractant. The extractant may be contained in a chamber of the container prior to testing and the end of the dipstick may be supported in the container out of contact with the extractant until testing is performed. For example, a chamber may be provided in the container between a closed end of the container and a membrane within the container, and the membrane may be ruptured to enable the milk or other fluid attached to the dipstick, and the extractant, to be brought into contact during testing. The membrane may be of plastic, or a metal or a combination of these such as for example only, metalized Mylar.

The dipstick may be moveable within the container from a position in which the dipstick is supported out of contact with the membrane, and a position in which the end of the dipstick is in contact with the extractant, such movement rupturing the membrane.

In one arrangement the dipstick may be supported by a cap which closes an open end of the container until removed, the cap including a frangible connection which is broken to enable the dipstick to move within the container to rupture the membrane. Thus the dipstick and the container are adapted for single use.

The cap of the container may include indicia means so that the container can be uniquely identified and readily indexed with an animal which produces the milk or other biological fluid sample. In one arrangement, such indicia means may include one or more wings on which information may be provided e.g. by writing.

The container is preferably tubular, but preferably is of a non-circular cross section and is receivable in a corresponding non-circular opening of the luminometer so that the container is constrained to a desired orientation in the opening e.g. to maximise light collection from the container.

The extractant may typically be a lysate, which ruptures the somatic cells in the fluid, on contact. Thus to facilitate the reaction, preferably the dipstick includes a reagent such as an enzyme to react with cellular components in the milk or other biological sample.

The dipstick most conveniently is made of a plastic material. To prevent neutralisation of the enzyme or other reagent carried on the dipstick by the material from which the dipstick is made, preferably a barrier is provided betwveen the agent and the material of the dipstick. In one arrangement, the agent may be carried on an absorbent pad which is adhered or otherwise secured to the dipstick. One such pad is an absorbent fabric pad made of cotton or other natural fibres for examples. Such a pad may be configured to absorb a known amount of milk or other fluid, so that a known amount of fluid is used in the test. The dipstick may be configured to encourage excess fluid not to attach to the dipstick. For example the end of the dipstick may be pointed.

One suitable reagent is firefly luciferin together with the enzyme luciferase.

The luminometer may be configured to count all photons emitted as a result of the luciferin/luciferase reaction or only photons in a particular frequency range. Thus all photons or only photons specific to the luciferin/luciferase chemical reaction may be sensed by the luminometer as desired.

According to a second aspect of the invention we provide a method of testing a biological sample from an animal for the presence of disease in the animal, the method including inserting an end of a dipstick into a sample of the biological fluid whereby a predetermined amount of the sample is attached to the dipstick, inserting the dipstick into a container whereby the predetermined amount of the sample takes part in a reaction in the container which produces light emissions, inserting the container into the luminometer and operating the luminometer to sense light emissions from the container and determining a level of bacteria in the sample and providing an output from the luminometer The method of the second aspect of the invention may utilise any of the features of the apparatus of the first aspect of the invention.

According to a third aspect of the invention we provide a dipstick assembly for use in an apparatus according to the first aspect of the invention, the assembly including a dipstick having a free end which is adapted to be dipped into a biological fluid sample, and to attach to the dipstick a predetermined amount of the sample for use in a subsequent reaction, characterised in that the sample is milk and the dipstick carries an agent which takes part in the subsequent reaction to provide light emissions.

The dipstick of the assembly may have any of the features of the dipstick of the apparatus of the first aspect of the invention.

According to a fourth aspect of the invention we provide in combination a container containing a test reagent and a biological fluid sample to be tested, and a luminometer device, the reagent and the sample reacting to produce light emissions, the luminometer being adapted to receive the container and to sense the light emissions, and wherein the container and the luminometer are adapted so that the container, when received in the luminometer, is received in a preferred orientation.

The reagent may be contained within the container by virtue of being attached to the dipstick.

For example the container may be elongate and of non-circular cross section, and the luminometer may include an opening of cross section corresponding to the cross section of the container. Thus the container may be orientated to maximise light collection and to ensure test consistency between different samples.

The container and/or the luminometer may have any of the features of the container and/or luminometer of the apparatus of the first aspect of the invention.

BRIEF DESCRIPTION OF THE DRAWINGS

The invention will now be described with reference to the accompanying drawings in which.

DETAILED DESCRIPTION OF THE PREFERRED EMBODIMENTS

Figure 1:
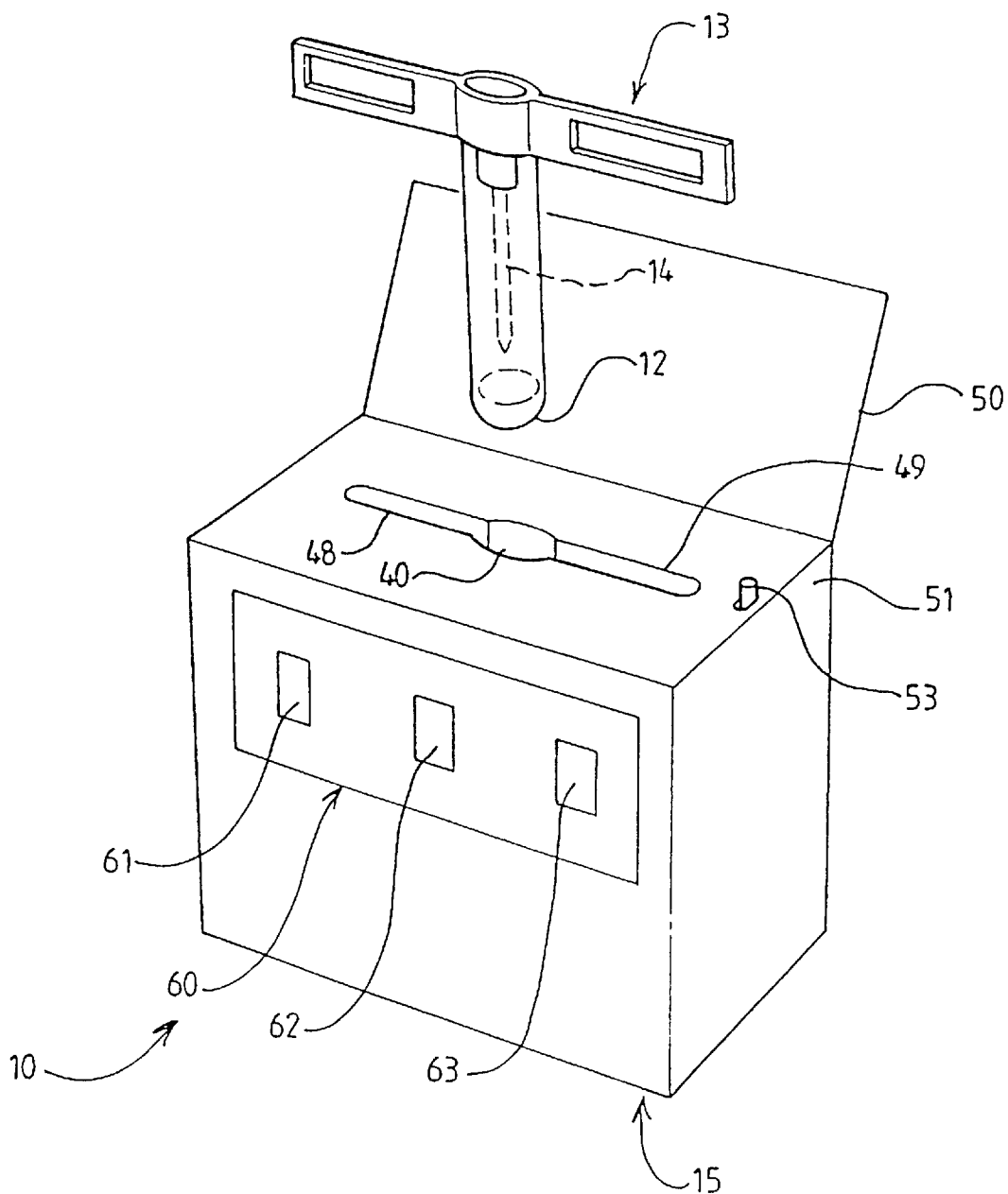
FIG. 1 is an illustrative view of a milk testing apparatus in accordance with the invention.

Referring to the drawings there is shown an apparatus 10 for testing milk to determine whether an animal which has produced the milk is suffering from a disease, particularly, mastitis.

The apparatus 10 includes a container 12 which receives a dipstick assembly 13 prior to use. The dipstick assembly 13 includes a dipstick 14 which in use of the apparatus 10 as described below, is dipped into a milk sample, is replaced in the container 12 and the container 12 containing the dipstick 14 is then placed in a luminometer 15 which senses light emissions from the container 12.

The container 12 in this example is a test-tube, made of a transparent material such as a suitable plastic or glass. Within the container 12 there is a membrane 16 which separates a closed end 17 of the container 12 from the remainder of the container 12 which has an open end 18.

Within a chamber 20 provided between the closed end 17 and the membrane 16, there is provided an extractant 21 in liquid form, the chemical make up and function of which will become apparent hereinafter. The extractant 21 is thus retained within the chamber 20, and preferably there is a space 22 within the chamber 20 which is un-filled with extractant 21, but contains air or an inert gas. In the example of suitable reagent to be described, it is preferred for the reagent to be oxygen saturated, and so if desired, the space 22 may contain an oxygen enriched gas, or even pure oxygen.

The membrane 16 may be made of a material which can readily be punctured/ruptured, for example a suitably thin plastic, metal or combination material such as metalised Mylar, polyethylene or polypropylene, for examples and only the membrane 16 is preferably positioned within the container 12 and sealed relative to the container 12, for example using an ultra-sonic sealing technique. Further alternatives, the membrane may be made of metal materials or even wax or cellulose acetate.

The container 12 is preferably of a non-circular configuration, but may otherwise be adapted as indicated below, so that the container 12 may be placed in a preferred orientation within the luminometer 15.

The open end 18 of the container 12 receives the dipstick assembly 13 which has a cap 25 which has a closure part 26 which serves both to mount the dipstick 14, and to co-operate with the container 12 to close the open end 18 thereof. Thus the closure part 26 of the cap 25 may be made of a suitable resilient plastics material and is preferably a push fit into the open end 18 of the container 12. The cap 25 includes in this example an indicia means 27 which is adapted to be labelled, e.g. by writing thereupon that the container 12 can be referenced with an animal whose milk is to be tested.

The indicia means 27 has in this example two wings 28, 29 which extend sideways from the closure part 26 and as well as providing a surface for labelling, may be adapted to co-operate with the luminometer 15 as described hereinafter to support the container 12 in the luminometer 15 during light emission sensing.

Figure 2:
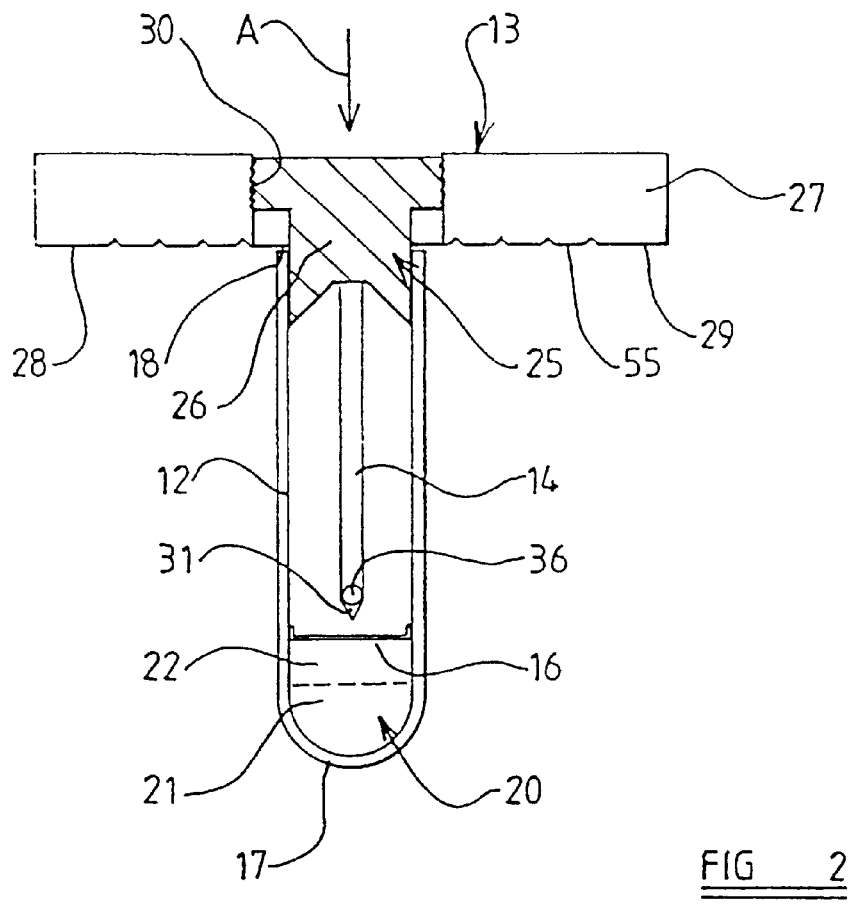
FIG. 2 is a detailed side view of part of the apparatus of FIG. 1.
Figure 3:
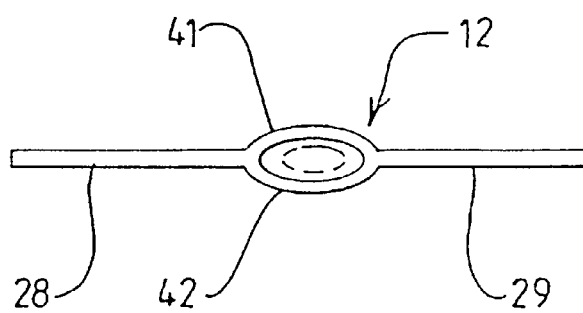
FIG. 3 is a plan view of the part of the apparatus shown in FIG. 2.

The closure part 26 of the cap 25 is attached to the indicia part 27 by means of a frangible connection 30, which retains the closure part 26 so that the dipstick 14 supported thereby is normally supported so that a free end 31 thereof is above the level of the membrane 16. However, the frangible connection 30 may be broken by applying pressure to the closure part 26 in the direction indicated by arrow A in FIG. 2, so that the free end 31 of the dipstick 14 may be pushed through the membrane 16 into contact with the reagent 21 within the chamber 20 at the closed end 17 of the container 12.

The dipstick 14 supported by the closure part 26 is preferably made of a suitable plastic material, but could be made of another suitable material as desired. The dipstick 14 is preferably adhered within an opening of the closure part 26, or may be retained as an interference fit only, or in another example, the dipstick 14 could be integrally made with the closure part 26 of the dipstick assembly 13.

The free end 31 of the dipstick 14 is of a pointed configuration. This is so that the free end 31 may easily puncture the membrane 16 when required, and also so that when the dipstick 14 is dipped into a milk sample, excess milk is encouraged to drip from the free end 31, so that only a predetermined amount of milk is used in testing.

The dipstick 14 carries a reagent which takes part in a chemical reaction during the test as hereinafter described. Typically the reagent includes an enzyme. Most preferably the reagent is a mixture of firefly luciferin and the enzyme luciferase.

Because the enzyme can be de-natured and neutralised if the enzyme comes into contact with the plastic material of the dipstick 14, preferably the agent is carried by a neutral carrier such as a fabric pad 36 which may be adhered, and/or mechanically secured and/or secured by heat staking relative to the dipstick 14. For example the pad 36 may be secured to the dipstick 14 by double sided adhesive tape. By such an arrangement, although any enzyme or other agent which is in intimate contact with the plastic of the dipstick 14 and/or with the adhesive of the double sided tape may be neutralised, a sufficient amount of the enzyme or other agent will be isolated to take part in the chemical reaction of the test.

In one arrangement the dipstick 14 may be made of a transparent plastic material such as transparent polycarbonate, so reducing the amount of light blockage caused by the dipstick, during luminometer 15 reading. Also the fabric pad 36 is flat thus presenting a maximum surface area to the light detector in the luminometer 15.

Because enzymes particularly but other agents too can degrade in the presence of oxygen, it is preferred for the closed container 12 above the membrane 16 to contain a neutral atmosphere. The container 12 above the membrane 16 may thus be at least partly evacuated although this could make removal of the dipstick assembly 13 from the container difficult, or the container 12 may contain an inert gas, such a nitrogen, or at least an inert gas rich gas. Thus the membrane 16 needs to be gas impermeable so that the oxygen rich gas in the space 22 of the closed end 17 does not permeate through or past the membrane 16 into the inert atmosphere in the remainder of the container 12.

This provides for improved shelf life and product stability. It is important that the activity of the enzyme is maintained so that consistent results can be obtained over the life of the product, which is expected typically to be a year or so.

The test method will now be described.

First the container 12 is opened by removing the dipstick assembly 13, using the wings 28, 29 of the indicia means 27 of the assembly 13 as handle, as required. This causes a break in a seal (not shown) between the closure part 26 and the container 12 to provide an obvious visual/tactile signal that the dipstick assembly 13 has been used, thus minimising the possibility of the dipstick 14 being inadvertently used a second time before being measured. Removal of the closure member 26 will release the inert atmosphere above the membrane 16 and expose the enzyme or other agent carried by the dipstick 14 to the atmosphere and thus this method step is preferably performed immediately before the other method steps. The free end 31 of the dipstick 14 is then dipped into a sample of milk to be tested. The sample is preferably obtained during milking, and thus is preferably specific to a single animal, as identified on the indicia means 27. Where desired the sample may be specific to a particular teat.

In each case, excess milk is allowed to drip from the dipstick 14, which preferably is retained in a free end 31 pointing downwards orientation, so that excess milk is encouraged to drip from the pointed free end 31.

The size of the fabric pad 36 carried by the dipstick 14 is arranged to ensure that a predetermined amount of milk becomes attached to the dipstick 14 and in contact with the enzyme or other agent on the pad 36.

Next the dipstick 14 is returned to the container 12, and the closure part 26 of the cap 25 is inserted into the container 12 with the free end 31 of the dipstick 14 to which the milk is attached, still out of contact with the reagent in the closed chamber 20 of the container 12.

A dairymen or other tester may collect samples from plurality of animals, and perform the method steps described above on each sample, using a different dipstick assembly 13 and container 12 for each sample. When all the samples required have been collected, and when convenient for the tester e.g. at the end of milking, the next method step may be performed.

For each container 12, the frangible connection 30 of the cap 25 may be broken to cause the pointed free end 31 of the dipstick 13 to puncture the membrane 16 and cause the attached milk and enzyme or other agent, to come into contact with the extractant 21. The container 12 being of generally constant cross section throughout the majority of its length, and the closure part 26 of the cap 25, will continue to co-operate as the dipstick 14 is moved to puncture the membrane 16, and to continue to support the dipstick 14 in its new position in the container 12.

The extractant 21 is a lysate and therefore, when the milk attached to the dipstick comes into contact with the extractant 21 (as it will, provided the container is maintained in a generally upright orientation), the somatic cells in the milk are lysed and ruptured. Lysis of the somatic cells results in a release of, among other things, adenosine triphosphate (ATP) from the cells. Each somatic cell contains approximately the same quantity of ATP and therefore the quantity of ATP released into the extractant 21 is dependent upon the number of somatic cells in the milk sample. The ATP, and the oxygen in the space 22 are catalysed by the luciferase to react with the firefly luciferin and emit photons.

The reaction will continue for some time, and so where the membrane 16 is punctured outside the luminometer 15, the container 12 may be placed in the luminometer 15 after the reaction begins.

Preferably though, the membrane 16 is punctured by the dipstick 14 in the luminometer 15. The luminometer 15 has an opening 40 therein to receive the container 12. The opening 40 is configured so that the container 12 may only be received in the luminometer 15 in a preferred orientation. In the example shown, the container 12 is generally elliptical or oval in cross section over a majority of its length, with the opening 40 of the luminometer 15 being of a corresponding configuration. Thus, one of the sides 41, 42 of the container 12 may be located close to a light sensor within the luminometer 15, and being flatter than a conventional round test-tube, light collection efficiency is maximised. Also, by arranging for the flat of the fabric pad 36 of the dipstick 14 to be aligned with the longer axis of the elliptical tube 12, the pad 36 will be orientated in the luminometer 15 with the flat of pad 36 facing the detector, to maximise the efficiency of light detection.

The wings 28, 29 of the indicia means 27 of the cap 25 are located in corresponding slots 48, 49 of the luminometer 15.

As lid 50 of the luminometer 15 is then closed preferably this action causes the dipstick 14 to be pushed down through the membrane 16. This may for example be achieved by the lid 50 having a pin or the like which pushes down on the centre of the closure member 26. Thus the cap design may be such as to make it difficult for a user manually to puncture the membrane 16 with the dipstick 14. As shown, preferably the lid 50 is hinged to a body 51 of the luminometer 15, and closing of the lid 50 also actuates a switch 53 whereby a light sensing sequence is initiated.

The luciferin/luciferase reaction is extremely sensitive and specific to the presence of ATP in the solution. Therefore, the intensity of light emitted as a result of the chemiluminescent reaction is directly related to the quantity of ATP in the solution. Since the quantity of ATP in solution is, in turn, directly related to the number of somatic cells in the milk sample, the intensity of the light emitted is directly related to the quantity of somatic cells in the milk sample. Because the fabric pad 36 carried by the dipstick 14 is arranged such that a predetermined amount of milk is attached to the pad 36, the concentration of somatic cells in the sample is also related to the intensity of the emitted light.

The luminometer 15 may be arranged to give a visual and/or aural indication when the light emission sensing commences and/or when the luminometer 15 has finished its sensing sequence. Preferably the luminometer 15 is calibrated to give an immediate indication of the results of the test. For example the luminometer 15 may include a display 60 of red, 61, amber 62, and green 63 lights, one of which lights up to indicate the test result. When green light 63 light up this may indicate that light emissions have been below a first predetermined level which indicates that only a low, normal, level of somatic cells are present in the milk sample, so that it may be concluded that the animal from which the milk has come does not have mastitis. When the amber light 62 lights up, this may indicate that the light emissions have been above the first predetermined level, but not above a second predetermined level which would indicate that a high level of somatic cells are present. Thus upon an amber readout, re-testing or further more detailed testing would be advisable. Then the red light 61 lights up, this would indicate an abnormal number of somatic cells above the second predetermined level are present in the milk sample, which would indicate disease in the animal. Because the milk is from a teat, the most likely disease indicated is mastitis. Upon a "red" result, the dairyman or other tester, can administer anti-biotic treatment and/or seek expert help from a vetenary practitioner.

Further features of the invention are as follows.

It will be appreciated that because the container 12 is sealed until the cap 25 is removed, and the cap 25 is sealed with the container 12 immediately after dipping, the risk of ingress of unwanted matter into the container 12 is minimised. Thus a tester can dip the dipstick 13 into a milk sample and return the dipstick to the container 12 quickly and easily, even in the conditions of a cowshed, without substantial risk of test contamination. The connection between the closure part 26 and the indicia means 27 may enable the closure part 26 to be removed from the container 12 by a simple pinching operation which may be performed one handed with the container 12 supported e.g. in a holster or the like which may conveniently be worn by the tester.

Because in the example described, a frangible connection 30 is broken to enable the free end 31 of the dipstick 14 to be brought into contact with the reagent 21, there is no risk of the container 12 of the apparatus 10 being inadvertently re-used, as it will immediately be apparent to the tester that the container 12 has already been used and it is not readily possible to return the dipstick 14 to its pre-testing position within the container 12.

If desired, the indicia means 27, or the container 12 otherwise, may be adapted to enable a specific milk sample to be identified automatically in the luminometer 15, so that the luminometer 15 may automatically index test results and provide a print out or electronic data output for use in a computer for example.

In the example shown, the indicia means 27 includes a plurality of notches 55, in the present example four notches 55. One or some or all of these notches 55 may be present or removed, and the luminometer 15 may include means to sense the presence and absence of notches 55 so that a particular indicia means 27 can be automatically identified. Other arrangements including bar coding, electronic tagging and the like may be used so that a correlation can be made by the luminometer 15 or in a computer to which data is transferred, between a test result and a test sample.

Various modifications may be made to the apparatus 10 described without departing from the invention.

For example, the container 12 need not be of the particular non-circular in cross section configuration described, but could be of an alternative non-circular or even circular configuration as desired. The cap 25 need not have an indicia means as shown at 27, but some other means of indexing a particular test container 12 with a particular animal to be tested may be used.

Instead of a frangible connection 30 between the closure part 26 and the remainder of the cap 25, other arrangements are possible which enable the dipstick 14 to be supported out of contact with the reagent 21 in the closed space of the container 12 until it is desired to perform testing.

In the example described, milk is attached to the dipstick 14 by means of the absorbent fabric pad 36 which also serves to isolate the enzyme or other agent carried by the dipstick 14, but the milk may otherwise be attached to the dipstick 14, although the arrangement described is preferred. By using an alternative chemiluminescent reaction dependant upon a cellular component of the somatic cells of the milk and a reagent on the dipstick, the use of an extractant in the container 12 may be avoided altogether. Alternatively, in another such chemical reaction, the use of a reagent 21 on the dipstick 14 may not be required, but a suitable reagent may be provided in the container 12 so that there is a reaction between the reagent and a cellular component of somatic cells in the milk, which produces light emissions for sensing using a luminometer 15.

The membrane 16 could in another example be wax, cellulose actuate, or metal such as aluminium or stainless steel.

The luminometer 15 may be adapted to handle several containers 12 at once, rather than a single container 12 as shown. The luminometer 15 may simply count photons of light emitted as a result of the chemical reaction between a reagent and a cellular component of somatic cells in the milk, or may differentiate between photons of different frequency so that only photons within a particular frequency/range emitted during a particular chemical reaction relevant to identifying somatic cells in the milk sample may be counted.

In another arrangement, rather than the indirect test described in which the level of somatic cells in a milk sample is used in an indicator of the level of bacteria in the milk, the apparatus 10 described above may be used, with appropriate reagent(s), to perform a direct test in which light emissions arising as a result of a chemical reaction between cellular components of bacterial cells and the reagent(s) are sensed.

The invention has been particularly but not exclusively developed for testing animals and may be applied not only to dairy cows but to any other milk producing mammal where it is desired to test the milk for signs that the animal is suffering from disease.

The invention may be adapted for the testing of other biological samples such as saliva, blood or urine, particularly where such tests are to be preferred routinely away from a laboratory environment.

It will be appreciated that throughout this specification the term "cellular component" is intended to mean not only proteins, but other components such as nucleic acids, oligosaccharides, fatty acids and any conglomerations or constituents of these or other cell content molecules and elements.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

What is claimed is:

1. An apparatus for testing a biological sample from an animal for the presence of disease in the animal, the apparatus comprising: a container having a rupturable membrane within the container; a dipstick having an end for insertion into the sample so that a predetermined amount of the sample becomes attached to the dipstick; the container including a chamber containing a reagent which, during testing, reacts with the sample attached to the dipstick to produce light emissions, the chamber being provided in the container between a closed end of the container and the membrane; the dipstick being movable within the container from a first position in which the dipstick is supported in the container out of contact with the membrane, and a second position in which the end of the dipstick with the attached sample is in contact with the reagent, the membrane being ruptured as the dipstick moves from the first position to the second position; and a luminometer for receiving the container, the luminometer having a lid which, on being closed, causes the dipstick to be moved from the first position through the membrane to the second position, whereby a determination of a level of bacteria and/or somatic cells in the sample and hence of the disease in the animal is made by sensing the light emissions from the container.

2. The apparatus according to claim 1, wherein the lid is further operative, on being closed, for activating the luminometer and commencing sensing of the light emissions from the container.

3. The apparatus according to claim 1, wherein the dipstick further includes a dipstick reagent which takes part in a reaction with the sample attached to the dipstick to create a light producing reaction.

4. The apparatus according to claim 3, wherein, to facilitate the light producing reaction, the dipstick reagent on the dipstick includes a mixture of luciferin and luciferase, the luciferin being catalyzed by the luciferase to react and emit light, in the presence of adenosine triphosphate, and that to prevent neutralization of the dipstick reagent carried on the dipstick by a material from which the dipstick is made, a barrier is provided between the dipstick reagent and the material of the dipstick.

5. The apparatus according to claim 4, wherein the dipstick reagent is carried on an absorbent pad which is secured to the dipstick.

6. The apparatus according to claim 1, wherein the reagent contained in the chamber of the container is an extractant to lyse cells in the biological sample and release the cell contents, the reaction being dependent upon one or more components of the cell contents.

7. The apparatus according to claim 1, wherein the dipstick is supported by a cap which closes an open end of the container until removed, the cap including a frangible connection which is broken to enable the dipstick to move within the container to rupture the membrane, the cap of the container further including an indicia device so that the container can be uniquely identified and readily indexed with the animal which produced the sample, the indicia device including one or more wings on which information is provided.

8. The apparatus according to claim 1, wherein the container is generally tubular and of a non-circular cross-section and is receivable in a corresponding non-circular opening of the luminometer.

9. The apparatus according to claim 1, wherein the end of the dipstick is pointed.

10. A method of testing biological fluid from an animal for the presence of disease in the animal, the method comprising the steps of: inserting an end of a dipstick into a sample of the biological fluid so that a predetermined amount of the fluid sample is attached to the dipstick; inserting the dipstick into a container, the container including a chamber provided between a closed end of the container and a membrane within the container; inserting the container into a luminometer, and closing a lid of the luminometer to cause the dipstick to move within the container through the membrane to rupture the membrane, and into the chamber, thus permitting the fluid sample to react with a reagent contained within the chamber and produce light emissions; and operating the luminometer to sense the light emissions from the container, determining a level of bacteria and/or somatic cells in the fluid sample, and providing an output from the luminometer.

* * * * *